(12) United States Patent
Lowe

(10) Patent No.: US 9,414,755 B2
(45) Date of Patent: Aug. 16, 2016

(54) METHOD FOR ESTIMATING A CENTRAL PRESSURE WAVEFORM OBTAINED WITH A BLOOD PRESSURE CUFF

(75) Inventor: Andrew Lowe, Auckland (NZ)

(73) Assignee: USCOM LTD., Sydney (AU)

( * ) Notice: Subject to any disclaimer, the term of this patent is extended or adjusted under 35 U.S.C. 154(b) by 1560 days.

(21) Appl. No.: 12/454,123

(22) Filed: May 13, 2009

(65) Prior Publication Data
US 2009/0287097 A1 Nov. 19, 2009

Related U.S. Application Data

(60) Provisional application No. 61/194,193, filed on Sep. 24, 2008, provisional application No. 61/214,962, filed on Apr. 30, 2009.

(51) Int. Cl.
*A61B 5/022* (2006.01)
*A61B 5/00* (2006.01)

(52) U.S. Cl.
CPC .............. *A61B 5/022* (2013.01); *A61B 5/02225* (2013.01); *A61B 5/411* (2013.01); *A61B 5/7239* (2013.01)

(58) Field of Classification Search
CPC ........ A61B 5/021; A61B 5/022; A61B 5/023; A61B 5/02208; A61B 5/02225
USPC ................................................. 600/490–494
See application file for complete search history.

(56) References Cited

U.S. PATENT DOCUMENTS

| | | | |
|---|---|---|---|
| 5,265,011 A | 11/1993 | O'Rourke | |
| 5,913,826 A | 6/1999 | Blank | |
| 6,331,162 B1 * | 12/2001 | Mitchell | 600/485 |
| 6,428,482 B1 | 8/2002 | Sunagawa et al. | |
| 6,647,287 B1 | 11/2003 | Peel, III et al. | |
| 6,712,768 B2 | 3/2004 | Ogura et al. | |
| 6,740,045 B2 | 5/2004 | Amano | |

(Continued)

OTHER PUBLICATIONS

Payne et al., Similarity between the suprasystolic wideband external pulse wave and the first derivative of the intra-arterial pulse wave, British Journal of Anaesthesia 99 (5): 653-61, 2007.*

(Continued)

*Primary Examiner* — Michael Kahelin
*Assistant Examiner* — Tho Tran
(74) *Attorney, Agent, or Firm* — Karl F. Milde, Jr.; Eckert Seamans Cherin & Mellott, LLC

(57) ABSTRACT

A physics-based mathematical model is used to estimate central pressure waveforms from measurements of a brachial pressure waveform measured using a supra-systolic cuff. The method has been tested in numerous subjects undergoing cardiac catheterisation. Central pressure agreement was within 11 mm Hg and as good as the published non-invasive blood pressure agreement between the oscillometric device in use and the so-called "gold standard." It also exceeds international standards for the performance of non-invasive blood pressure measurement devices. The method has a number of advantages including simplicity of application, fast calculation and accuracy of prediction. Additionally, model parameters have physical meaning and can therefore be tuned to individual subjects. Accurate estimation of central waveforms also allow continuous measurement (with intermittent calibration) using other non-invasive sensing systems including photoplethysmography.

33 Claims, 12 Drawing Sheets

(56) References Cited

U.S. PATENT DOCUMENTS

| | | |
|---|---|---|
| 6,746,405 B2 | 6/2004 | Narimatsu |
| 6,786,872 B2 | 9/2004 | Narimatsu et al. |
| 6,793,628 B2 | 9/2004 | Ogura et al. |
| 6,802,814 B2 | 10/2004 | Narimatsu |
| 6,808,496 B2 | 10/2004 | Oka et al. |
| 6,814,705 B2 | 11/2004 | Kawaguchi |
| 6,976,966 B2 | 12/2005 | Narimatsu |
| 7,326,180 B2 | 2/2008 | Tanabe et al. |
| 7,468,037 B2 | 12/2008 | Illyes et al. |
| 2002/0038090 A1 | 3/2002 | Sunagawa et al. |
| 2004/0059232 A1* | 3/2004 | Narimatsu ............... 600/494 |
| 2004/0077959 A1 | 4/2004 | Narimatsu |
| 2006/0224070 A1* | 10/2006 | Sharrock et al. .......... 600/500 |

OTHER PUBLICATIONS

Berend Westerhof et al., Arterial Pressure Transfer Characteristics: Effects of Travel Time (Am J Physiol Heart Circ Physiol 292:800-807, 2007.).

Berend Westerhof et al., Individualization of Transfer Function in Estimationof Central Aortic Pressure from the Peripheral Pulse is Not..(J Appl Physiol 105:1858-1863, 2008).

Physical Basis of Pressure Transfer from Periphery to Aorta: A Model-Based Study, AJP—Heart 274: 1386-1392, 1998.

* cited by examiner

METHOD FOR ESTIMATING A CENTRAL PRESSURE WAVEFORM OBTAINED WITH A BLOOD PRESSURE CUFF

CROSS-REFERENCE TO RELATED APPLICATION

This present application claims benefit of priority from U.S. Provisional Application No. 61/194,193, filed Sep. 24, 2008 and U.S. Provisional Patent Application No. 61/214, 962, filed Apr. 30, 2009. The invention disclosed and claimed herein is related in subject matter to that disclosed in U.S. Pat. No. 5,913,826, issued Jun. 22, 1999; U.S. Pat. No. 6,994,675, issued Feb. 7, 2006; and the aforementioned U.S. Patent Publication No. 2006/0224070-A1 and U.S. Patent Publication No. 2009/0012411-A1, all of which are incorporated herein by reference.

BACKGROUND OF THE INVENTION

The present invention relates to a method of measurement of suprasystolic waveforms from an upper-arm blood pressure cuff. The analysis and interpretation of these waveforms can be performed directly on the measured and processed signals. It has been demonstrated that the suprasystolic waveform changes significantly and predictably with the administration of vasoactive agents, physiological challenges, normal ageing processes and morbidities.

Recent literature has noted the potential importance of central blood pressure (waveform and values such as systolic, diastolic and mean) in the management of cardiovascular risk. To that end, it would be advantageous to be able to estimate central pressures.

More particularly, the invention relates to methods of physics-based modelling of the waveform measurement system and the arterial system being studied. One of the early models of this kind, constructed by Joe El-Aklouk at the Institute of Biomedical Technologies, Auckland University of Technology, was based on acoustic pressure wave propagation in tubes.

El-Aklouk's work involved the development of models to simulate wave propagations given known material properties, geometry, end conditions and driving inputs. El-Aklouk also studied the transmission of pressure oscillations in an artery to an externally applied inflatable cuff.

More recent models have been proposed by Berend Westerhof et. al. (Am J Physiol Heart Circ Physiol 292:800-807, 2007.) who examined the pressure transfer between the subclavian root and unoccluded brachial artery assuming that the more peripheral arteries present a known end-impedance. In another recent paper (J Appl Physiol 105:1858-1863, 2008), Westerhof et al. attempt to show that changes in impedance caused by changes in the peripheral circulation have a negligible effect on the central pressure prediction. Westerhof et al. do not consider the use of a suprasystolic cuff to isolate the brachial artery from the peripheral circulation.

SUMMARY OF THE INVENTION

A principal object of the present invention is to improve the estimation of central pressure waveform by applying a suprasystolic cuff and using an inverse brachial-artery to cuff-pressure model.

A more particular object of the present the present invention is to extend the theoretical work done by El-aklouk and Westerhof et al. to include a derivation of an inverse model and specifically apply it to the subclavian-brachial arterial branch. This inverse model allows the prediction of the driving input pressure (in the aortic arch) from the measurement of supra-systolic waveform. It has been found that the inverse model problem can be costly and iterative numercical methods. asolution has been derived with assumptions to allow presentation in a closed-form. The model utilises only physically meaningful parameters.

This model according to the invention has been applied to clinical data collected in a study of subjects undergoing cardiac catheterisation at Auckland City Hospital, led by Dr. Wil Harrison. The results of this study, which validate the model, are set forth hereinbelow.

Model Derivation

In the arterial system under consideration, a pressure wave propagates through a volume of blood enclosed by the left subclavian and brachial arteries. At the brachial end, the artery is essentially closed by the application of a suprasystolic blood pressure cuff.

A number of assumptions, along with their justifications, have been made, as follows:

The artery is circular in cross section. MRI imaging has shown this to be essentially correct.

The artery has parallel sides. The radius change between the subclavian root and brachial artery is approximately 1.5 millimeters over a distance of 400 mm.

The arterial cylinder is thin walled, that is, the wall thickness is much less than the internal radius. The artery wall thickness reported in the literature is approximately $\frac{1}{8}^{th}$ the radius.

The blood flow velocity is much less than the speed of sound. That is, kinetic-to-potential energy conversion is negligible. Also, the viscoelastic properties of blood flow can be ignored. Under conditions of a suprasystolic cuff with consequent artery occlusion, there is essentially no blood flow within the artery.

There are no bifurcations within the artery segment. The left subclavian-brachial conduit is essentially free from bifurcations (although there are a number of small branches). The next major bifurcation is the branching of the brachial artery in to the radial and ulnar arteries. This occurs more distally than the suprasystolic cuff.

The end conditions of the artery segment can be described as an abrupt change in impedance. Finite element models show the transition to the closed state under the suprasystolic cuff happens over the space of a few millimeters. Likewise, the subclavian root branches abruptly from the aortic arch, which is of much larger diameter.

There is no hydrostatic pressure differential along the artery. Medical practice advises that non-invasive measurements are taken with the cuff approximately level with the heart. This assumption therefore holds.

Note that many of these assumptions do not hold for other measurement methods. In particular, the use of an arterial line or tonometry method does not allow the assumption of a constant, abrupt change in impedance, nor of zero blood flow. Measurement at a radial site also introduces a significant bifurcation into the arterial system being studied, as well as further compromising the thin-walled tube assumption. Note also that the model is most correct for the left arm. The right subclavian artery is one branching generation removed from the aorta.

Using the above assumptions, it can be demonstrated that pressure propagation in the system can be described by the acoustic wave equation in one dimension:

$$\frac{\partial^2 p_t}{\partial x^2} - \frac{1}{c^2} \frac{\partial^2 p_t}{\partial t^2} = 0$$

where $p_t$ is the acoustic pressure (local deviation from ambient pressure), c is the speed of sound, x is the spacial coordinate and t is time.

$$c = \sqrt{\frac{Eh}{2\rho r}}$$

where E is the elastic modulus of the artery wall material, h is wall thickness, r is tube radius and $\rho$ is blood density.

Given a constant arterial cross section, the speed of sound is constant in time and space, and so the general solution can be described by $$p_t = p_p(x - c\,t) + p_n(x + c\,t)$$

where $p_p$, $p_n$ represent positive- and negative-going pressure waves respectively, the total pressure $p_t$ being a superposition of the two component waves.

It is also known that at an impedance change (causing a change in the speed of sound) a portion of a wave will be reflected, and a portion (the remainder) of the wave will be transmitted.

Using this information, the following relationships between the total pressure in the aorta and the total pressure at the occlusion may be written, for the system depicted in FIG. 1:

$$P_{t0}(s) = \frac{e^{-dts}(a + e^{2dts})P_{t2}(s)}{1 + a}$$

$$p_{t0}(t) = \frac{a}{1+a} p_{t2}(t - dt) + \frac{1}{1+a} p_{t2}(t + dt)$$

where subscripts 0, 1 and 2 respectively represent locations in the aorta outside the subclavian artery (source), the root of the subclavian artery and just before the occlusion. Factor a is the reflection coefficient at the cuff and is physically constrained to be in the range 0 to 1. Constant dt is the time taken for a wave to travel from the subclavian root to the cuff occlusion.

It can be seen that under the conditions and assumptions described above, which are specific to suprasystolic measurement, theoretically, the aortic pressure waveform can be easily reconstructed from the occlusion pressure, using only two parameters, a and dt.

Measurement Model

The formulation thus far has considered only the internal physics of pressure wave propagation within the artery. The sensing system according to the invention is, however, non-invasive and relies on the transfer of internal pressure oscillations to an externally applied inflatable cuff.

It has been reported in the literature that the amplitude of the transferred pressure oscillation is determined by a large number of factors. However, the critical parameter appears to be the transmural pressure—that is, the difference in pressure between the externally applied cuff pressure and the internal arterial pressure. This relationship is shown diagrammatically in FIG. 2, which shows that the maximum relative amplitude is transferred at zero transmural pressure. As absolute transmural pressure increases, less oscillation is observed at the cuff. Given an approximately constant cuff pressure, as is the case with suprasystolic measurement, it is seen that the transmural pressure will change over the cardiac cycle.

This information permits compensation of the oscillometric waveform to estimate the arterial pressure. The procedure described herein is presented as a functional example, and may not be the only or even the best method of compensation.

The suprasystolic waveform, after filtering, $p_{osc}$, represents cuff pressure oscillations less than a few mmHg in amplitude. This waveform is rescaled to the measured systolic, SBP, and diastolic, DBP, pressures to generate $p_{ss}$.

$$p_{SS} = \frac{p_{Osc} - \mathrm{Min}(p_{Osc})}{\mathrm{Max}(p_{Osc}) - \mathrm{Min}(p_{Osc})}(SBP - DBP) + DBP$$

The difference between $p_{ss}$ and the cuff pressure, $p_{Cuff}$, is calculated to be the transmural pressure, $p_{tp}$. In the case of suprasystolic measurement the cuff pressure can be assumed to be a value 25 mmHg above SBP.

$$p_{TP} = p_{Cuff} - p_{ss}$$

A correction amount, $p_\Delta$ is calculated as a function of the transmural pressure. In order to match the relationship shown in FIG. 2, the correction amount should be zero at zero transmural pressure, and increase by increasing amounts as transmural pressure increases. These requirements can be met by a function of the form $$p_\Delta = (d\, p_{TP})^4$$

where d is a scaling factor.

Other forms of correction may also be applied. It has been found from our analysis that the form of correction should be such that if the corrected and uncorrected waveforms are normalized, then the correction function should be monotonically increasing between zero and one, but proportionally greater for pressures between zero and one, as shown in FIG. 12.

One function that satisfies this requirement is of the form $$p_{Corr} = \frac{-1 + d + p_{SSnorm}}{1 + d + p_{SSnorm}}$$

where $p_{SSnorm}$ is the uncorrected normalized waveform value, $p_{Corr}$ is the corrected normalized waveform value and d is a control parameter that controls the amount of correction.

Once the correction amount has been calculated, the estimated arterial pressure, $p_{Art}$, can be rescaled as follows $$p_{Corr} = p_{SS} + p_\Delta$$

$$P_{Art} = \frac{p_{Corr} - \mathrm{Min}(p_{Corr})}{\mathrm{Max}(p_{Corr}) - \mathrm{Min}(p_{Corr})}(SBP - DBP) + DBP$$

An example of an estimated pressure wave (normalized to SBP=1, DBP=0) is shown in FIG. 3.

Blood Pressure Scaling

In the above discussion, $p_{Art}$ was scaled to the measured systolic and diastolic pressures. In fact, the theory suggests that this is not a correct treatment. The arterial blood pressure is actually generated by wave reflections from the peripheral circulation. However, the arterial pressures estimated by suprasystolic measurement are a function of reflections from the cuff. The arterial pressures with a suprasystolic cuff will therefore likely be higher than the pressures without a suprasystolic cuff. The degree to which this is the case may depend on a number of factors. In this model, the scaling is treated as a constant factor, c.

$$p_{t2} = c\,(P_{Art} - \text{Mean}(p_{Art}))$$

Note once again that $p_{t2}$ is the pressure perturbation about a mean pressure, not the gauge blood pressure. The assumptions infer that the mean pressure does not change along the length of the subclavian-brachial artery. Therefore the aortic blood pressure can be estimated by the equation:

$$p_{AO} = p_{t0} + \text{Mean}(p_{Art})$$

Model Summary

In summary, the present invention is a model-based method of predicting central aortic pressures (specifically at the opening to the left subclavian artery). The input to the model is the suprasystolic, oscillometric waveform. The model has the following parameters:
- a: Absolute value of the reflection coefficient at the cuff. a ∈ (between 0 and 1);
- dt: Time for the pressure wave to propagate from the subclavian root to the occluding cuff (greater than 0 seconds);
- d: Scaling factor for transmural coupling correction; and
- c: Scaling factor for suprasystolic pressure waveform.

BRIEF DESCRIPTION OF THE DRAWINGS

FIG. 4 presents a comparison of oscillometrically determined brachial systolic blood pressure (SBP), and measured aortic SBP.

FIG. 5 presents a comparison of oscillometrically determined brachial diastolic blood pressure (DBP), and measured aortic DBP.

FIG. 7 presents a prediction of central systolic blood pressure using the model according to the invention and measured central systolic blood pressure.

FIG. 8 presents a prediction of central diastolic blood pressure using the model according to the invention and measured central diastolic blood pressure.

FIG. 9 shows a prediction of central Augmentation Index (AI) using the model according to the invention and measured central Augmentation Index.

DESCRIPTION OF THE PREFERRED EMBODIMENTS

Clinical data collected in a study of subjects undergoing cardiac catheterisation at Auckland City Hospital, led by Dr. Wil Harrison, were used to experimentally verify the theory and model according to the present invention.

Clinical Validation

Data for clinical validation was collected under the leadership of Dr. Wil Harrison from the cardiac investigation laboratories at Auckland City Hospital. Twenty-seven subjects were recruited from consecutive cases, with the exclusion of those with known, severe aneurysms, moderate to severe arrhythmias, or abnormal subclavian/brachial anatomy. Suprasystolic, oscillometric waveforms were collected non-invasively using a blood pressure cuff and analyzed using the model according to the present invention. Concurrently, ten seconds of invasive pressure waveforms were collected with the catheter tip near the aortic root. The non-invasive blood pressure (NIBP) was measured with a monitor using its internal, Welch Allyn oscillometric NIBP module. NIBP was determined approximately thirty seconds prior to the collection of waveform data.

Of the twenty-seven subjects recruited, technical difficulties prevented measurements from being taken on two of the first subjects. Poor quality catheter tracings were recorded on a further two subjects. Catheter tracings for one additional subject were not available at the time of this analysis. Waveform measurements were obtained from the remaining twenty-two subjects with a mean (sd) signal to noise ratio, SNR, of 13.4 (3.06) dB. This represents very good signal quality.

Non-Invasive vs. Invasive Measurements

As a point of reference, the statistics derived directly from the non-invasive and invasive measurements were compared.

Figure 1:
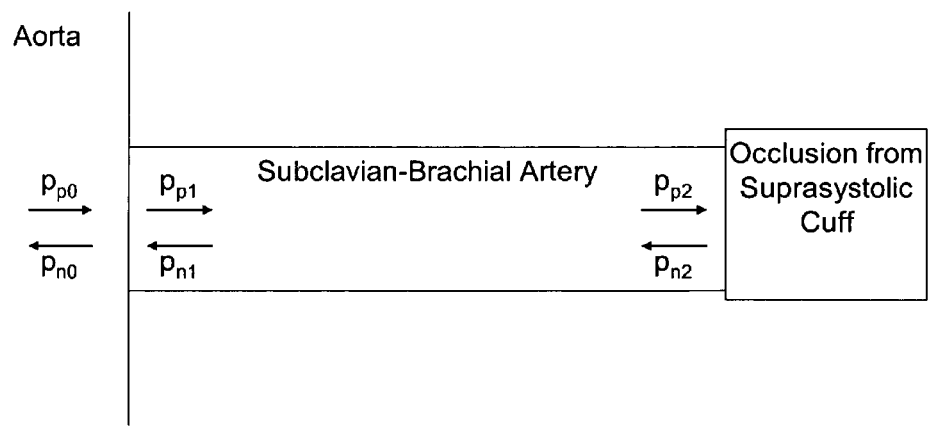
FIG. 1 is a diagram representing a model of an arterial system according to the present invention.
Figure 2:
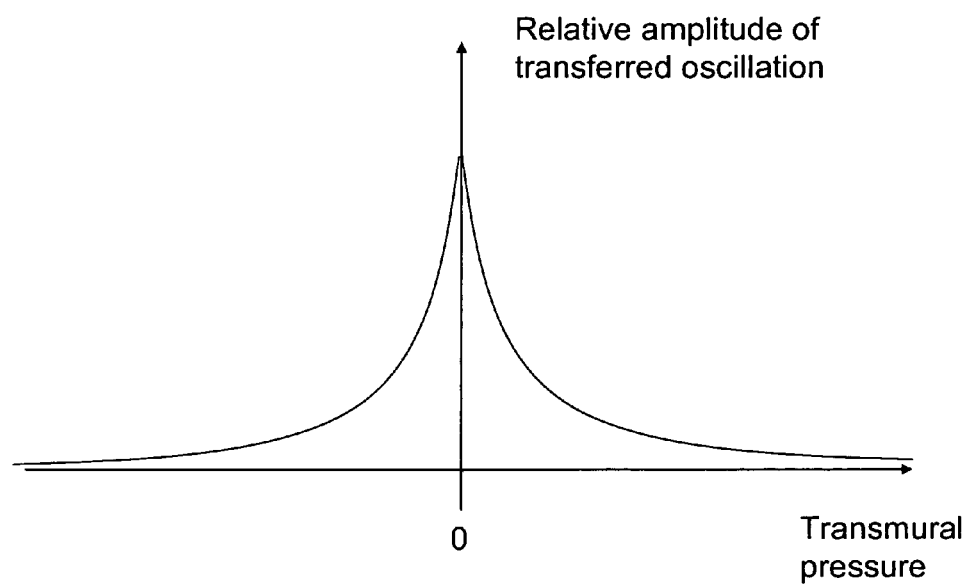
FIG. 2 is a diagram showing oscillatory response of the model according to the invention.
Figure 3:
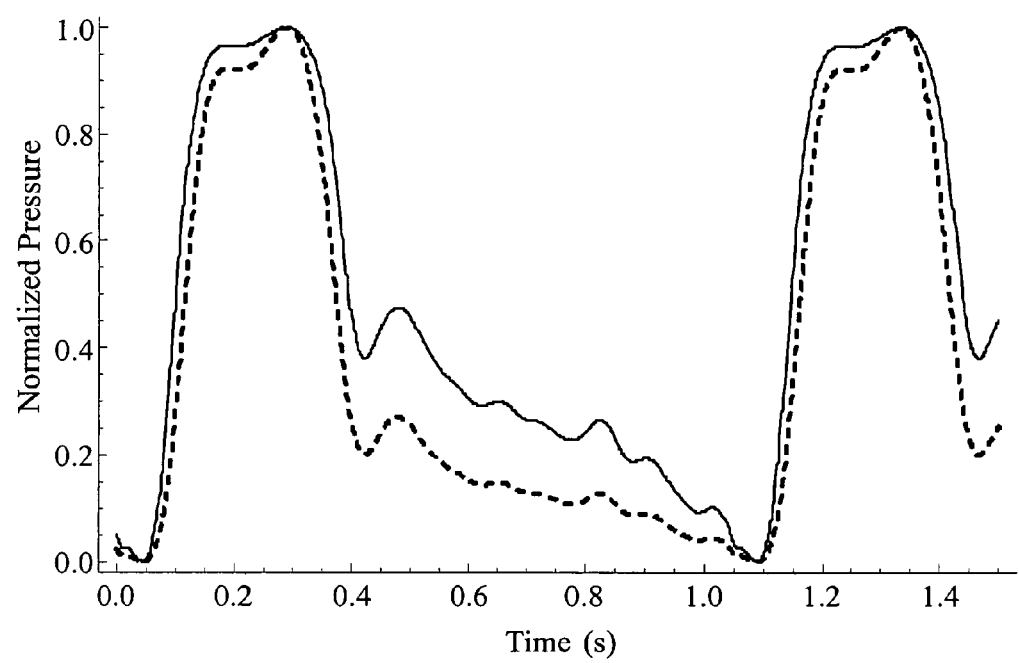
FIG. 3 is a time diagram showing a corrected pressure wave (upper line) and an original wave (lower line) in the model according to the invention.
Figure 4A:
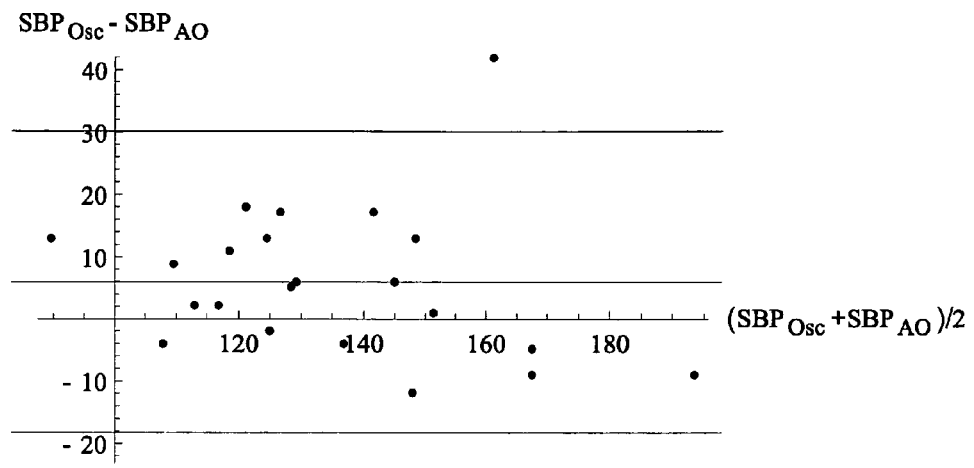
FIG. 4A is a Bland Altman Plot and FIG. 4B is an X-Y plot.
Figure 4B:
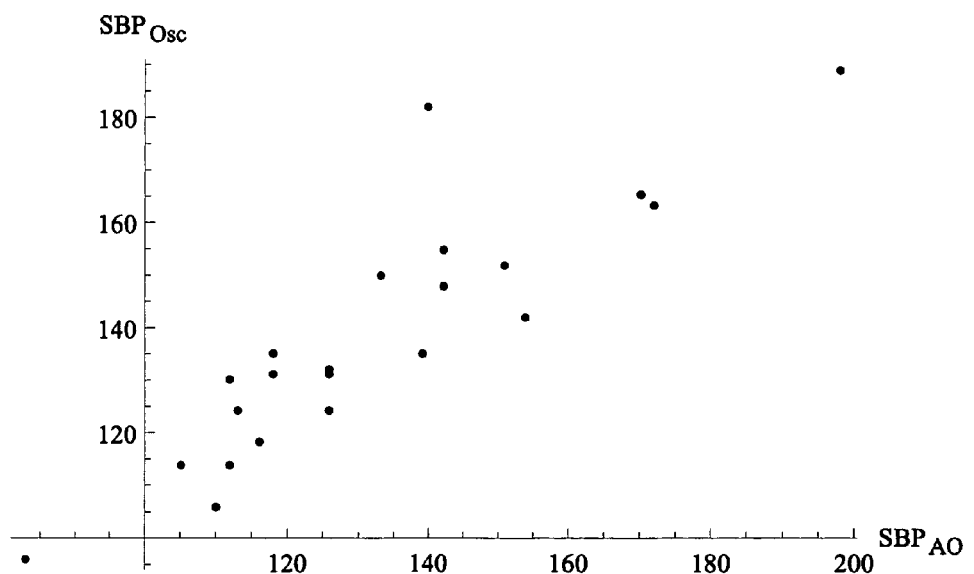

FIG. 4 shows agreement and correlation between oscillometric systolic pressure and measured invasive systolic pressure. Pearson's correlation coefficient, r, was 0.88. However, the limits of agreement (twice the standard deviation of the difference between paired measurements) are 5.9±24.2 mm Hg. This means that approximately 95% of measurements will be accurate within these limits. Clinically, such wide limits of agreement and significant bias indicate that non-invasive systolic pressure is a poor estimator of the central systolic pressure.

Figure 5A:
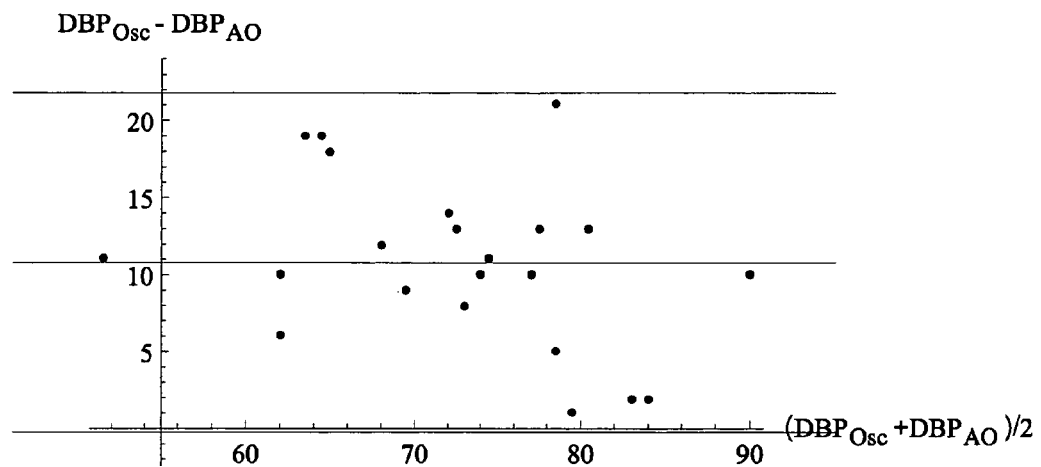
FIG. 5A is a Bland Altman Plot and FIG. 5B is an X-Y plot.
Figure 5B:
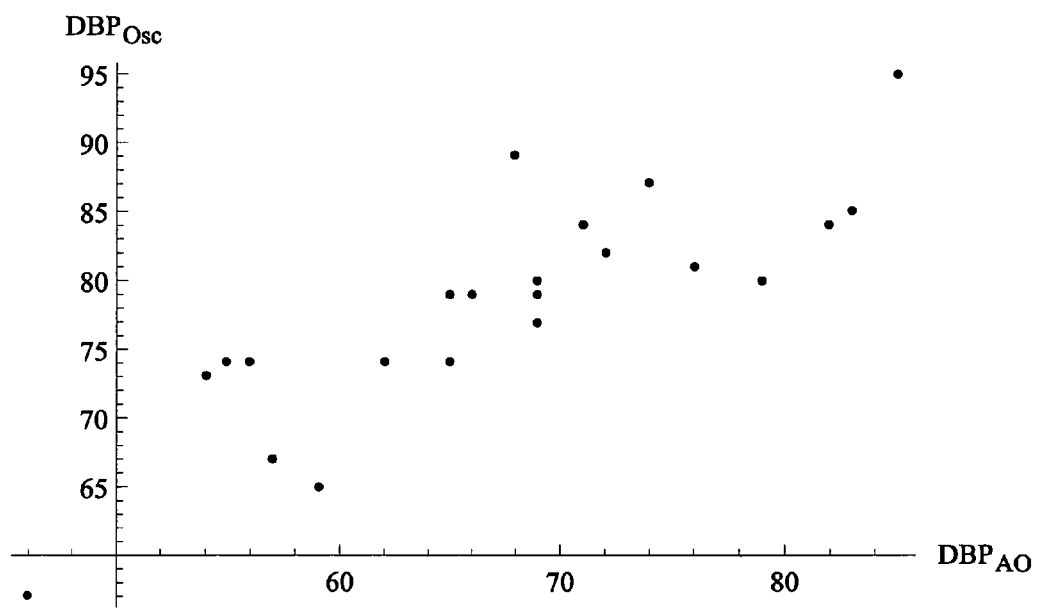

In the case of diastolic pressure, as shown in FIG. 5, the limits of agreement are somewhat tighter being 10.7±11.0 mmHg. However, the average bias is large. Correlation is comparable, with r=0.84.

Figure 6:
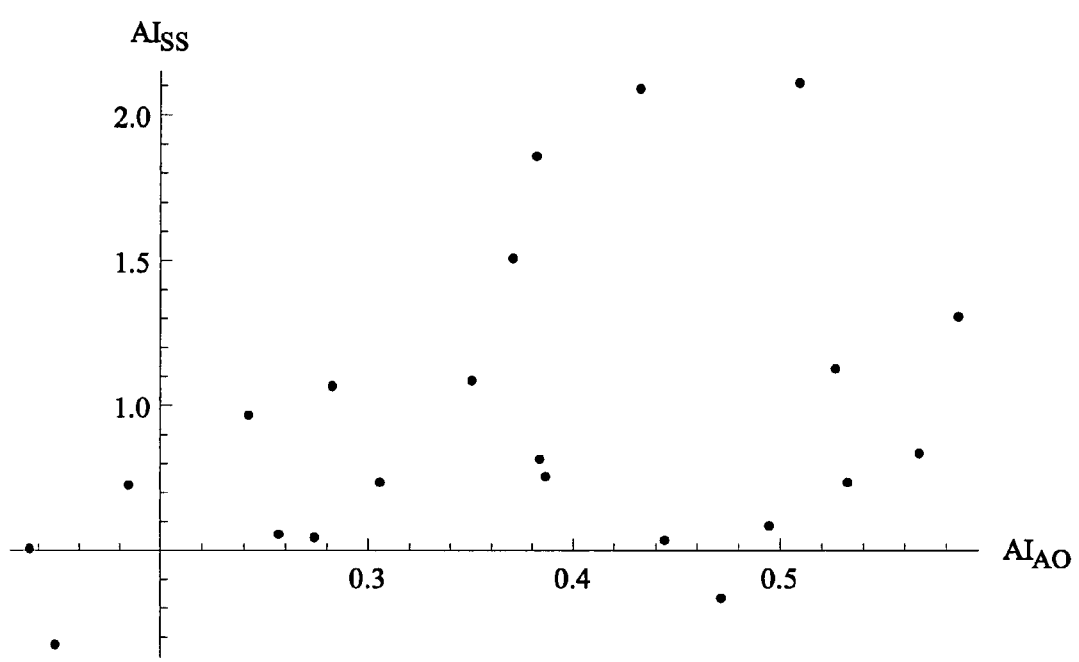
FIG. 6 shows a correlation of a suprasystolically measured brachial Augmentation Index (AI), and invasively measured AI.

Direct comparison between suprasystolic augmentation index as calculated by the R6.5 device ($AI_{SS}$) and central Augmentation Index AI is not justifiable due to the different method of calculation. However, if performed, it gives very poor limits of agreement of 57±94% and r of 0.56. The X-Y plot is shown in FIG. 6.

Model-Predicted vs. Measured Invasive Measurements

The model described above was applied to the clinical data in an investigation into the feasibility of predicting central pressures. Model parameters were set as follows: a=0.7, c=1.25, dt=0.045 seconds and d=0.045.

Figure 7A:
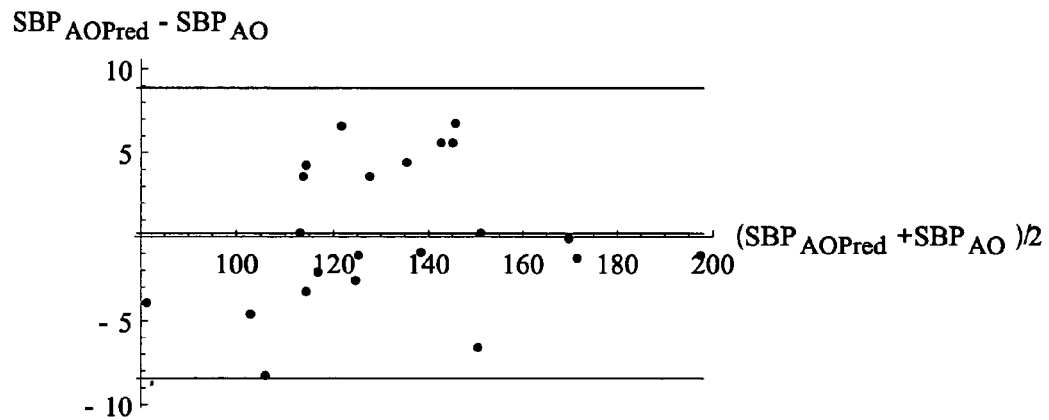
FIG. 7A is a Bland Altman chart and FIG. 7B is an X-Y chart.
Figure 7B:
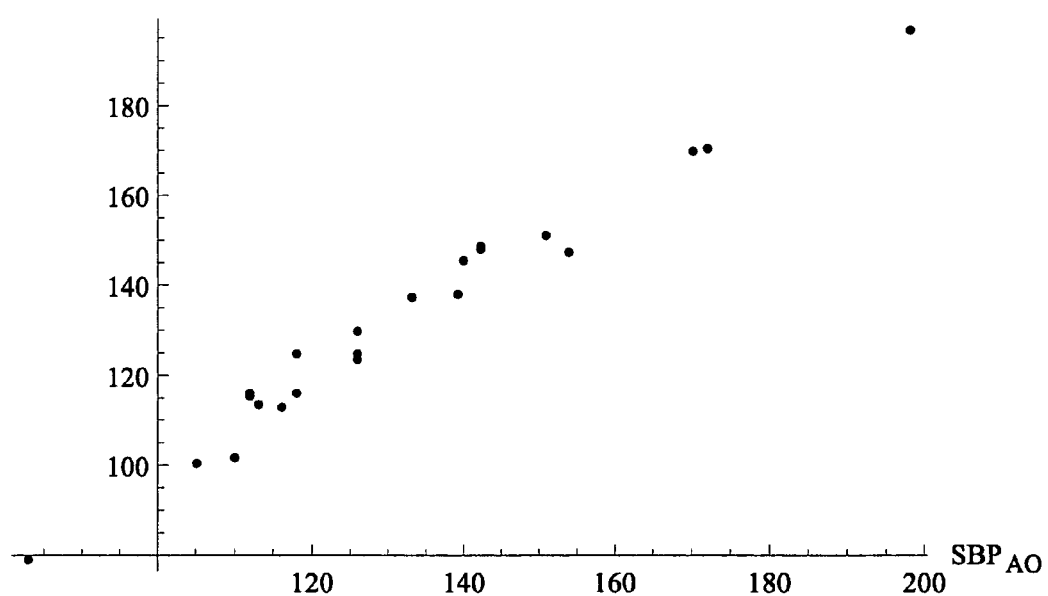

As can be seen in FIG. 7, central systolic pressures show much better agreement than directly comparing non-invasive pressures. The limits of agreement are 0.2±8.7 mmHg, with correlation coefficient r of 0.98. These limits of agreement should be considered in light of results published by Welch Allyn on the accuracy of the NIBP module being used, for which the limits of agreement are 2±11 mmHg.

Figure 8A:
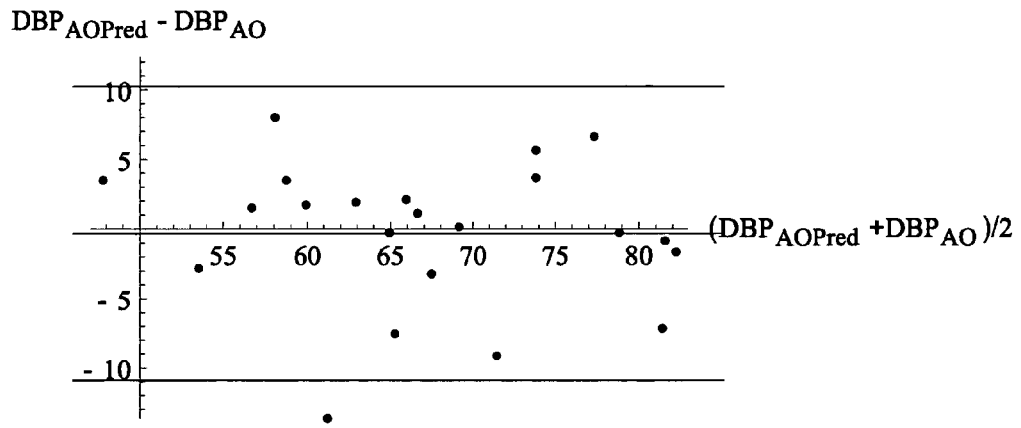
FIG. 8A is a Bland Altman chart and FIG. 8B is an X-Y chart.
Figure 8B:
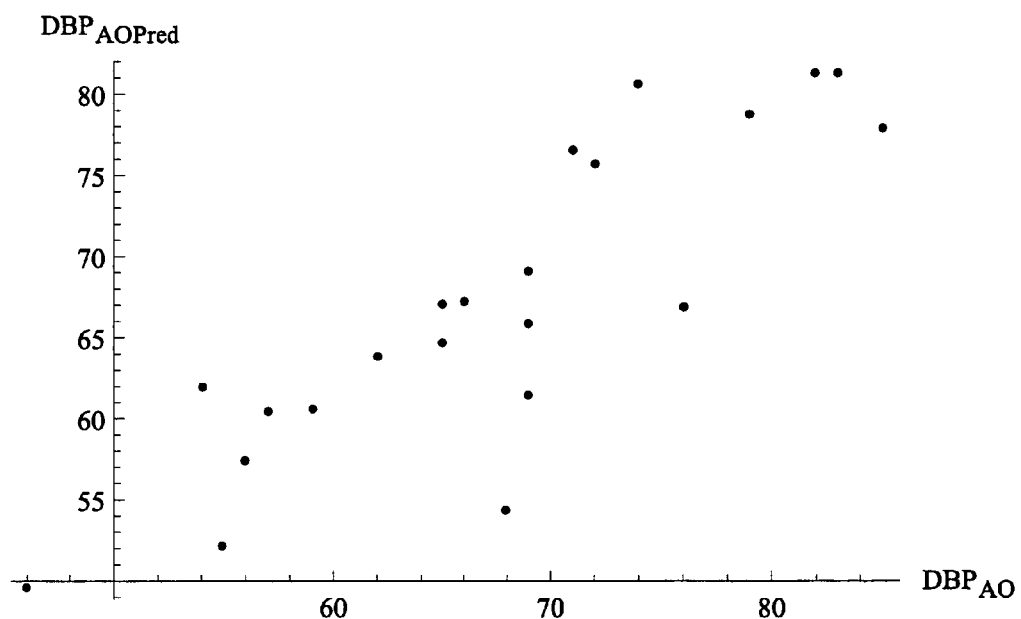

Similar results were obtained for diastolic blood pressure as shown in FIG. 8. The limits of agreement for the prediction are −0.3±10.6 mmHg. For comparison, the limits of agreement for Welch Allyn non-invasive diastolic pressure are −0.5±11 mmHg.

Figure 9A:
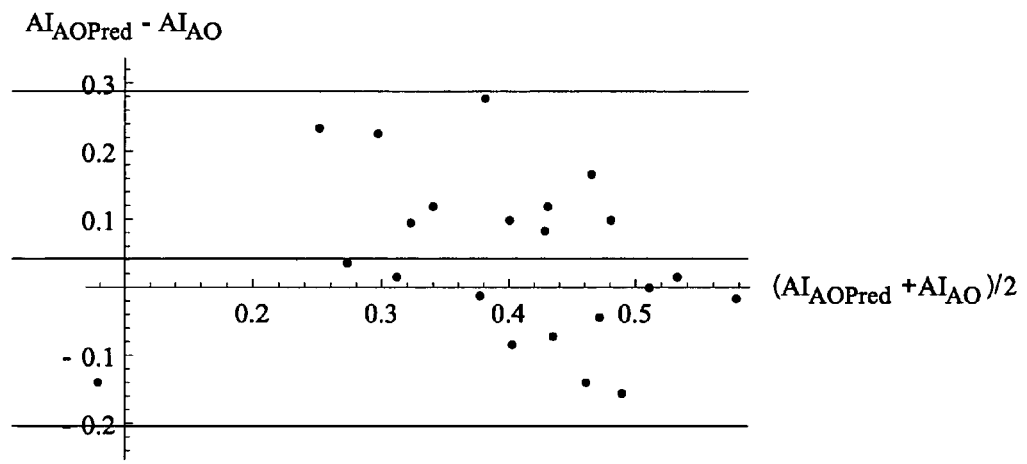
FIG. 9A is a Bland Altman chart and FIG. 9B is an X-Y chart.
Figure 9B:
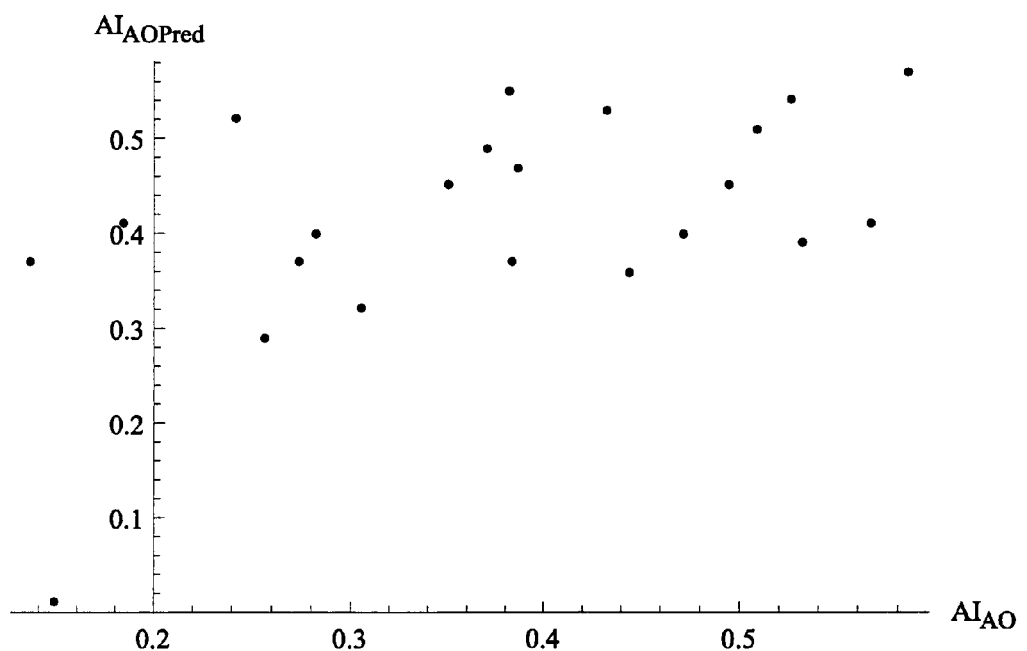

The invasive and predicted augmentation indices were also compared. The relevant charts are shown in FIG. 9. The limits of agreement are 4.1±24.6% and the correlation coefficient is 0.54.

Results of Clinical Study

It may be seen that the prediction of the central pressures using the model and method according to the present invention closely matches the actual values that were measured invasively. The method according to the invention does not require any calibration to central waveform parameters (such as diastolic and mean pressures). In view of the documented inaccuracies of the NIBP estimation, it appears that the central pressure variations cannot be significantly improved. Indeed, the blood pressure predictions easily pass the international standards for the accuracy of blood pressure devices (although this standard does not strictly apply to central pressure estimation).

There are a few methodological shortcomings to the current study, which are described below.

Central pressures were measured at the aortic root, whereas the model predicts pressures at the entrance to the left subclavian artery, which is situated near the top of the aortic arch.

A single NIBP determination was used for each patient. An idea of the variability introduced could be obtained by multiple, consecutive measurements, or by invasive measurement.

Model parameters were determined somewhat arbitrarily. A better approach would have been to estimate them from an independent set of data, or through mathematical modelling.

Identification of the anacrotic notch on measured invasive waveforms was open to debate in seven of the twenty-two subjects. This may explain some of the variability in agreement between model-predicted and measured augmentation index.

Ideally, parameters to the model would be determined by measurement of each individual subject. In the case of dt, this could be determined relatively easily using additional, non-invasive sensors, or possibly estimated from demographic information such as age, height, weight and sex. An analysis of the correlation between the derivative of the predicted waveform and the derivative of the measured waveform shows that this correlation is far more sensitive to parameter dt than to a. This is shown in FIG. 10 for a specific subject, but the overall shape of this surface is typical.

Figure 10:
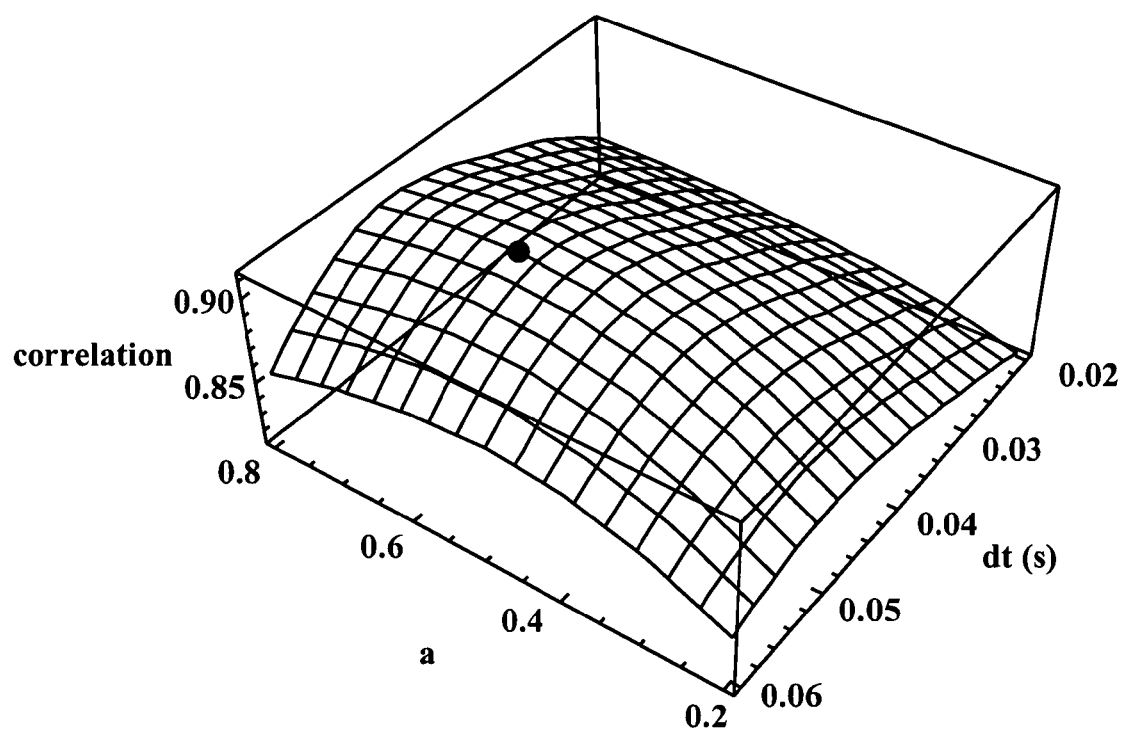
FIG. 10 shows a correlation between first derivatives of measured and predicted waveforms as a function of model parameters.
Figure 11A:
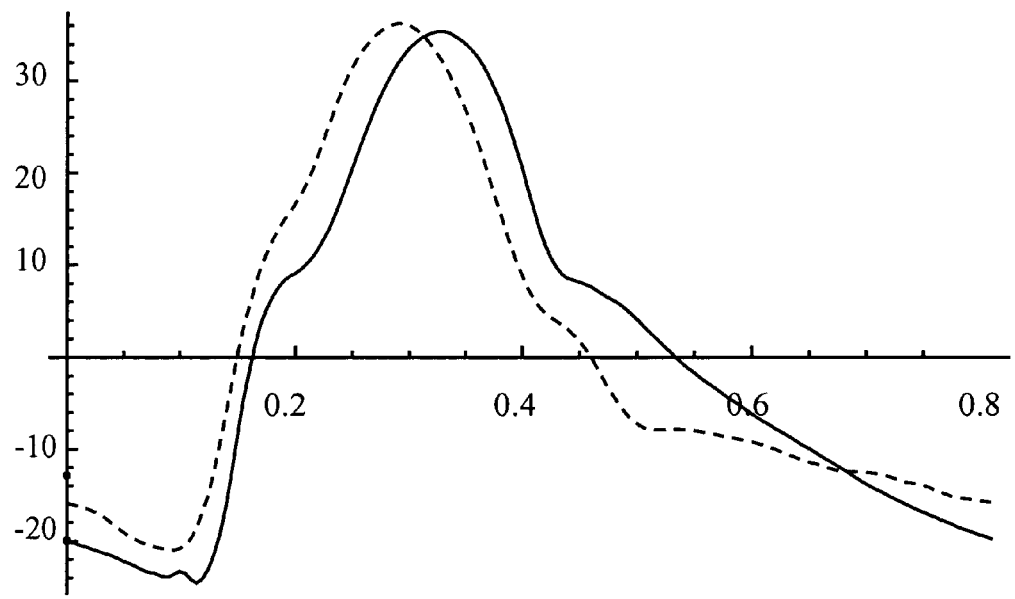
FIG. 11 shows a time series for the measured (solid line) and predicted (dashed line) pressure deviation from mean (FIG. 11A) and first derivative of pressure deviation (FIG. 11B).
Figure 11B:
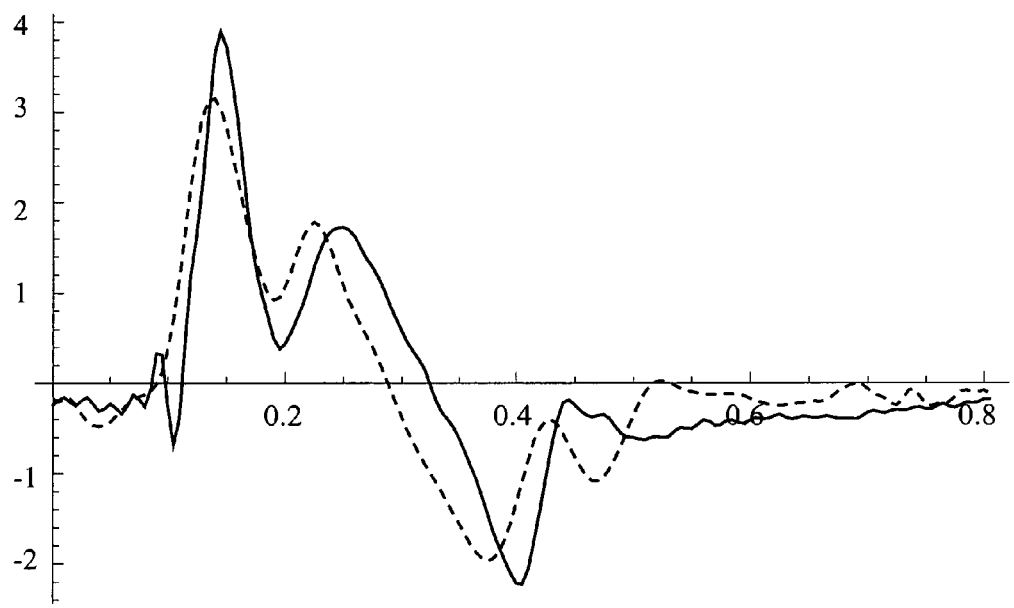
Figure 12:
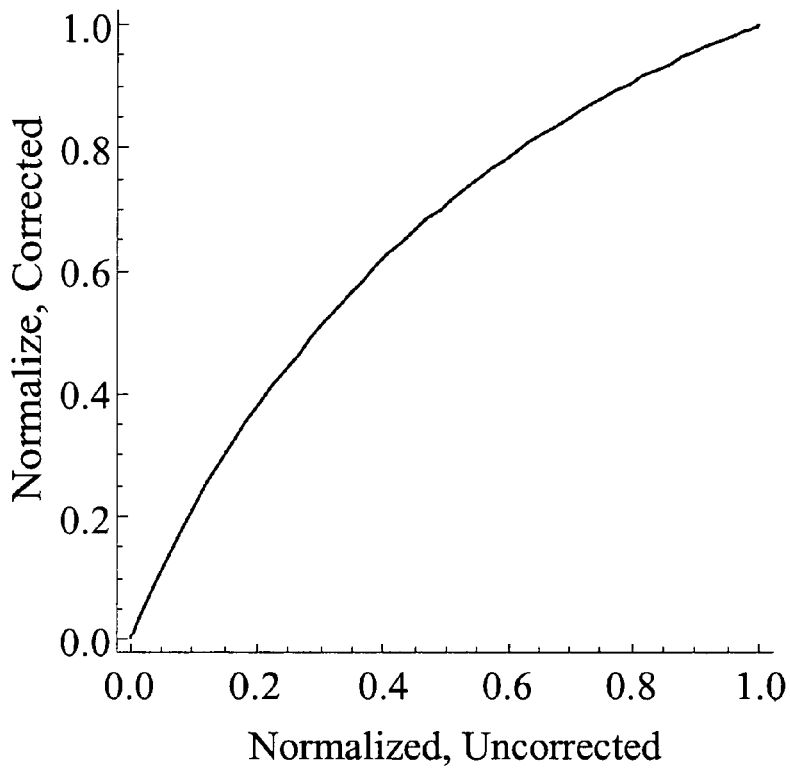
FIG. 12 shows a monotonically increasing relationship between the normalized, uncorrected cuff pressure waveform and the normalized, corrected, brachial artery waveform.

Note that the correlation shown in FIG. 10 is for the first derivative of the waveform. The correlation between predicted and measured waveforms was greater than 0.97. The corresponding time series are shown in FIG. 11.

Conclusions

The method according to the invention advantageously includes the steps of:
Non-invasive measurement of pressure waveforms;
The use of a suprasystolic blood pressure cuff;
The blood pressure measurement from the left brachial artery; and
The specific mathematical model presented above.

The method thus estimates central artery pressures and pressure waveforms from measurement of pressure pulse wave signals at a peripheral location using a blood pressure cuff.

Figure 14:
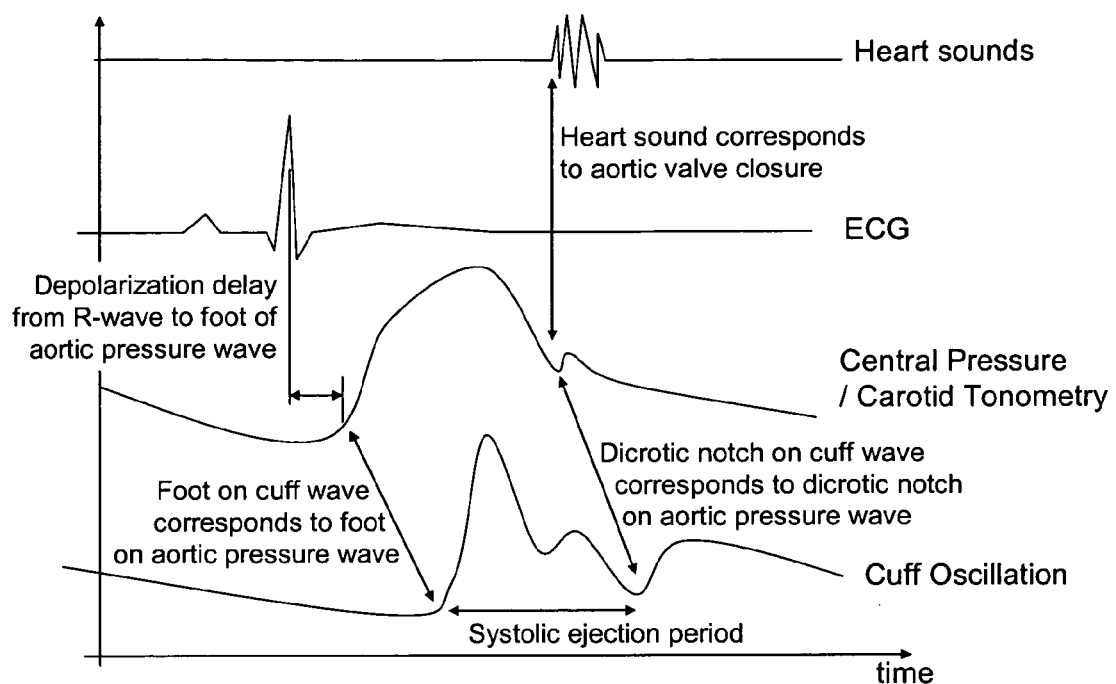
FIG. 14 is a time diagram of a single cardiac ejection cycle showing the timing of heart sounds, ECG pulses, central pressure and cuff oscillation waveforms.

The basic applications of this method are:
The imposition of known impedance end-conditions on a section of an artery downstream of a central artery. In this example, the suprasystolic cuff causes an occlusion, and isolates the section of artery on the distal side of the cuff.
The measurement of a heart-pulse synchronous signal from the section of artery between the known end condition and the central artery.
A method of calculation based on a mathematical model relating the heart-pulse synchronous signal and central pressure at the root of the peripheral artery.
A method of estimating the parameters to the mathematical model. These may be estimated based on previously measured data, characteristics of the patient (such as age, weight, height) and/or measurements taken from the subject. For example, with reference to FIG. 14:
A heart-sounds sensor may be used to estimate the time of entry of a pressure pulse into the subclavian artery. By assuming the systolic ejection period as measured on the cuff pressure wave is the same as for the central waveform, the time of entry of the pressure pulse is estimated by subtracting the systolic ejection period from the time of the heart sound corresponding to aortic valve closure.
The R-wave of an ECG can be assumed to occur a constant increment of time before the ejection of stroke volume, and therefore estimate the time of the foot of the central pressure wave.
If the left carotid artery is applanated concurrently with one suprasystolic cuff measurement, the time of the foot of the applanation wave can be considered to be nearly synchronous with the entry of the pressure wave into the subclavian artery.
A method of applying the mathematical model to estimate the central pressure from measured waveforms.

There has thus been shown and described a novel method for estimating a central pressure waveform obtained with a blood pressure cuff, which method fulfils all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

Figure 13:
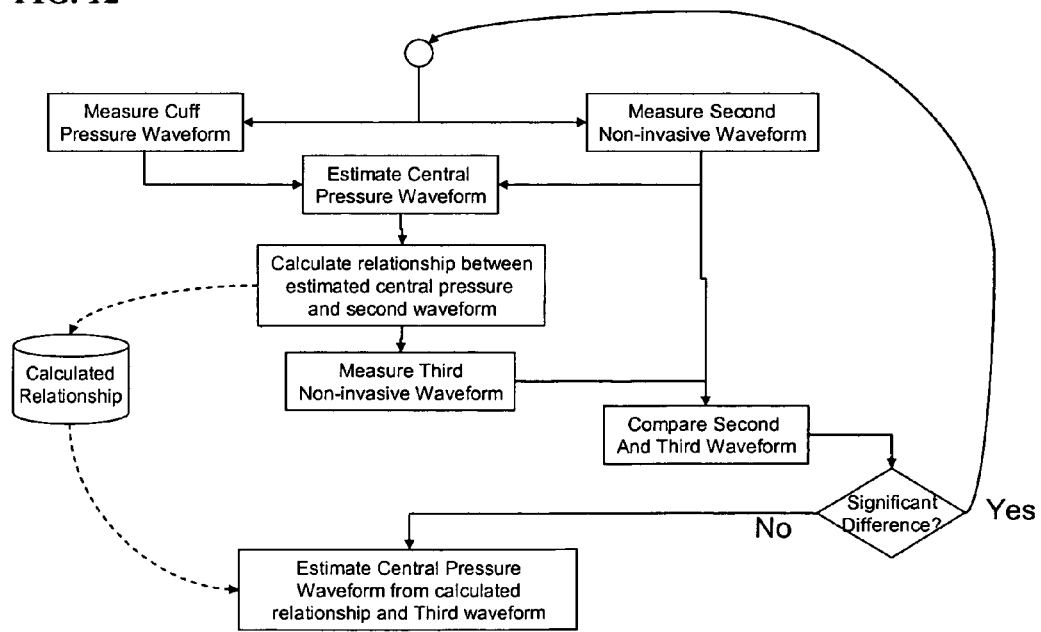
FIG. 13 is a flow chart of a method for non-invasively calibrating the central pressure waveform.

For example, additional aspects of the invention may include:
The estimated central waveform can be used to calculate a transfer function between estimated central pressure and another heart pulse synchronous signal. This second signal (for example, a finger photoplethysmograph or PPG) could be measured from another section of a peripheral artery with or without the imposition of the known impedance end-condition. In this way, the PPG signal could be used to continuously estimate central or peripheral pressure waveforms. Recalibration by the central-pressure waveform estimating means can occur at preset intervals, triggered by the clinician, or when characteristics of the measured waveform change. This algorithm is illustrated in FIG. 13.

The estimated central waveform can be used in conjunction with another heart pulse synchronous signal and a further mathematical model or transfer function to estimate characteristics of blood flow, including cardiac output.

What is claimed is:

1. A method of sensing and analyzing supra-systolic blood pressure waveforms obtained non-invasively from a brachial artery in an arm of a patient, using a blood pressure cuff and cuff pressure transducer, to estimate central artery blood pressures, said method comprising the steps of:
   (a) applying and inflating a blood pressure cuff on the patient's arm to a supra-systolic pressure;
   (b) using a non-invasive sensor, sensing a succession supra-systolic cuff pressure waveforms associated with the brachial artery in said patient's arm, each supra-systolic cuff pressure waveform forming a heart-pulse synchronous cuff pressure signal representing at least one cardiac ejection cycle;
   (c) using a computer, analyzing the supra-systolic cuff pressure waveforms using a first mathematical model relating the heart-pulse synchronous cuff pressure signal and brachial pressure near the cuff on said patient's arm to produce an estimated brachial pressure signal representing estimated brachial pressure waveforms, wherein the heart-pulse synchronous cuff pressure signal is scaled relative to previously measured systolic and diastolic pressures, such that the amplitude of the estimated brachial pressure signal is a proportion of a difference between the previously measured systolic and diastolic pressures;
   (d) using a computer, analyzing the estimated brachial pressure waveforms using a second mathematical model relating the estimated brachial pressure signal and a central pressure at the root of the brachial artery to produce estimated central artery blood pressures and estimated central artery blood pressure waveforms, whereby the second mathematical model includes at least one parameter with physical meaning selected from a group consisting of (a) an impedance relationship at the cuff and (b) a parameter relating a phase of a pressure wave at substantially the subclavian root to a phase of a supra-systolic pressure wave at the occluding cuff; and
   (e) generating a computer output representing estimated central artery blood pressures based on the analysis.

2. The method according to claim 1, wherein the systolic and diastolic blood pressures are measured using the blood pressure cuff on said patient's arm before, during or after the measurement of said supra-systolic cuff pressure waveforms.

3. The method according to claim 1, further comprising a correction step such that estimated brachial pressures between maximum and minimum estimated brachial pressures are corrected by a non-linear function, with said non-linear function monotonically increasing from the min to the maximum estimated brachial pressures, but being proportionally greater for pressures between the maximum and minimum estimated brachial pressure.

4. The method according to claim 1, wherein, according to the second mathematical model relating the estimated brachial pressure signal and central pressure at the root of the brachial artery, the estimated central artery blood pressure is a sum of a first proportion of the estimated brachial pressure signal shifted forwards in time by a propagation time, and a second proportion of the estimated brachial pressure signal shifted backwards in time by the propagation time, whereby the first proportion is a ratio of reflection coefficient at the cuff to the reflection coefficient plus one, and the second proportion is the ratio of one to the reflection coefficient plus one.

5. The method according to claim 3, wherein the correction step is of a form such that the corrected pressure estimate, if scaled between zero and one, equals a ratio of (a) a control variable minus one plus an uncorrected pressure scaled between zero and one to (b) the control variable plus one plus the uncorrected pressure scaled between zero and one, whereby the control variable controls an amount of non-linear correction.

6. The method according to claim 4, wherein the reflection coefficient at the cuff is assumed to be a predetermined constant.

7. The method according to claim 4, wherein the reflection coefficient at the cuff is determined based on an estimated change in artery cross section as a result of the application of a supra-systolic pressure to the blood pressure cuff.

8. The method according to claim 7, wherein the determination of the reflection coefficient depends upon a predetermined relationship between an estimated unoccluded artery size, the supra-systolic cuff sure and the previously measured systolic and diastolic pressures.

9. The method according to claim 4, wherein the propagation time is assumed to be a predetermined constant.

10. The method according to claim 4, wherein the propagation time is determined by an estimate of artery length and pulse wave speed made using a predetermined relationship with respect to at least one parameter of a patient, selected from the group consisting of gender, age, height, upper arm circumference, and brachial Augmentation Index.

11. The method according to claim 4, further comprising the step of measuring the propagation time in the brachial artery.

12. The method according to claim 11, wherein the propagation time is the difference in time between an occurrence of a foot. of the estimated brachial pressure pulse and an occurrence of a preceding R-wave of a synchronously collected ECG signal.

13. The method according to claim 11, wherein the propagation time is the difference in time between an occurrence of an foot of the estimated brachial pressure pulse and an occurrence of an foot of a simultaneously collected carotid tonometric signal.

14. The method according to claim 11, wherein propagation time is a difference in time between an occurrence of a dichrotic notch in the estimated brachial pressure pulse and a time of a heart sound corresponding to closure of an aortic valve simultaneously collected from a heart sound sensor.

15. The method according to claim 1, wherein the output of the analysis is a central systolic blood pressure.

16. The method according to claim 1, wherein the output of the analysis is a central diastolic blood pressure.

17. The method according to claim 1, wherein the output of the analysis central pulse pressure.

18. The method according to claim 1, wherein the output of the analysis is central Augmentation Index.

19. The method according to claim 1, wherein the output of the analysis is the maximum rate of change of central pressure with time.

20. The method according to claim 1, wherein the output of the analysis is central systolic ejection period.

21. The method according to claim 1, wherein the impedance relationship at the cuff is a reflection coefficient.

22. The method according to claim 1, wherein the impedance relationship at the cuff is a frequency response function.

23. The method according to claim 1, wherein the impedance relationship at the cuff is a digital filter.

24. The method according to claim 1., wherein the parameter relating the phase of the pressure wave at substantially the subclavian root the phase the supra-systolic pressure wave at the occluding cuff is a propagation time.

25. The method according to claim 1, wherein the parameter relating the phase of the pressure wave at substantially the subclavian root to the phase of the supra-systolic pressure wave at the occluding cuff is a frequency response function.

26. The method according to claim 1, wherein the parameter relating the phase of the pressure wave at substantially the subclavian root to the phase of the supra-systolic pressure wave at the occluding cuff is a digital filter.

27. A method analyzing central blood pressure waveforms obtained non-invasively from a brachial artery in an arm of a patient, using a blood pressure cuff and cuff pressure transducer as a first non-invasive sensor and as a second non-invasive sensor of heart synchronous pulse signals, thereby to estimate central artery blood pressures, said method comprising the steps of
 (a) applying and inflating a blood pressure cuff on the patient's arm to a supra-systolic pressure;
 (b) sensing a first succession of supra-systolic cuff pressure waveforms associated with the brachial artery in said patient's arm using the first non-invasive sensor, each supra-systolic cuff pressure waveform forming a heart-pulse synchronous cuff pressure signal representing at least one cardiac ejection cycle;
 (c) using a computer, analyzing the supra-systolic cuff pressure waveforms using a first mathematical model relating the heart-pulse synchronous cuff pressure signal and brachial pressure near the cuff on said patient's arm to produce an estimated brachial pressure signal representing estimated brachial pressure waveforms;
 (d) using a computer, analyzing the estimated brachial pressure waveforms using a second mathematical model relating the estimated brachial pressure signal and a central pressure at the root of the brachial artery to produce estimated central artery blood pressures and estimated central artery blood pressure waveforms, whereby the second mathematical model includes at least one parameter with physical meaning selected from a group consisting of (a) an impedance relationship at the cuff and (b) a parameter relating a phase of the pressure wave at substantially the subclavian root to a phase of a supra-systolic pressure wave at the occluding cuff;
 (e) sensing a second succession of heart-pulse synchronous cuff pressure signals using the second non-invasive sensor approximately corresponding in time to the first succession of supra-systolic cuff pressure waveforms;
 (f) using a computer, calculating a mathematical relationship relating the estimated central artery blood pressures to the second succession of heart-pulse synchronous cuff pressure signals;
 (g) deflating the blood pressure cuff to a sub-diastolic pressure;
 (h) sensing a third succession of heart-pulse synchronous cuff pressure signals using the second non-invasive sensor;
 (i) using a computer, determining the central artery blood pressures by using the previously calculated mathematical relationship relating the estimated central artery blood pressures to the second succession of heart-pulse synchronous cuff pressure signals and to the third succession of heart-pulse synchronous cuff pressure signals from the second non-invasive sensor; and
 (j) generating a computer output representing estimated central artery blood pressures based on the analysis.

28. The method according to claim 27, wherein the second non-invasive sensor of heart-pluse synchronous cuff pressure is a photoplethysmograph sensor.

29. The method according to claim 27, wherein the second noninvasive sensor of heart synchronous pulse signals is a tonometric sensor.

30. The method according to claim 27, wherein the second non-invasive sensor of heart synchronous pulse signals is a blood pressure cuff applied to another limb of the patient.

31. The method according to claim 27, wherein the mathematical relationship relating the estimated central artery pressures to the second succession of pulse signals is that of a transfer function.

32. The method according to claim 27, wherein the mathematical relationship relating the estimated central artery pressures to the second succession of heart-pulse synchronous cuff pressure signals is that of a digital filter.

33. The method according to claim 27, further comprising the step of comparing a difference between the third succession of heart-pulse synchronous cuff pressure signals from the second non-invasive sensor and the second succession of heart-pulse synchronous cuff pressure signals the second non-invasive sensor against predetermined criteria, and, if the difference should meet said predetermined criteria, performing another measurement according to the method of claim 27 to recalibrate the relationship between the second non-invasive sensor signal and the estimated central blood pressure.

* * * * *